US009725327B2

(12) United States Patent
Mertens et al.

(10) Patent No.: US 9,725,327 B2
(45) Date of Patent: Aug. 8, 2017

(54) MFI WITH UNUSUAL MORPHOLOGY

(71) Applicants: EXXONMOBIL CHEMICAL PATENTS INC., Baytown, TX (US); Machteld Maria Wilfried Mertens, Boortmeerbeck (BE); Marc H. Anthonis, Hofstade (BE); Antonie Jan Bons, Kessel-lo (BE); Brita Engels, Begijnendijk (BE); Wilfried Jozef Mortier, Kessel-lo (BE); Jane Chi-ya Cheng, Bridgewater, NJ (US)

(72) Inventors: Machteld Maria Wilfried Mertens, Flemington, NJ (US); Marc H. Anthonis, Hofstade (BE); Antonie Jan Bons, Kessel-Lo (BE); Brita Engels, Begijnendijk (BE); Wilfried Jozef Mortier, Kessel-Lo (BE); Jane Chi-ya Cheng, Bridgewater, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/440,946

(22) PCT Filed: Nov. 14, 2013

(86) PCT No.: PCT/EP2013/073816
§ 371 (c)(1),
(2) Date: May 6, 2015

(87) PCT Pub. No.: WO2014/082862
PCT Pub. Date: Jun. 5, 2014

(65) Prior Publication Data
US 2015/0298982 A1 Oct. 22, 2015

Related U.S. Application Data

(60) Provisional application No. 61/730,848, filed on Nov. 28, 2012.

(51) Int. Cl.
*C01B 39/40* (2006.01)
*B01J 29/40* (2006.01)
(Continued)

(52) U.S. Cl.
CPC .............. *C01B 39/40* (2013.01); *B01J 20/18* (2013.01); *B01J 29/40* (2013.01); *C07C 5/52* (2013.01);
(Continued)

(58) Field of Classification Search
CPC C01B 39/40; B01J 20/18; B01J 29/40; C07C 5/52; C07C 2529/44; C07C 2529/46; C07C 2529/48
See application file for complete search history.

(56) References Cited

U.S. PATENT DOCUMENTS

| 3,702,886 A | 11/1972 | Argauer et al. |
| RE29,948 E | 3/1979 | Dwyer et al. |

(Continued)

FOREIGN PATENT DOCUMENTS

| CN | 101733143 A | 6/2010 |
| EP | 0 174 121 | 3/1986 |

(Continued)

OTHER PUBLICATIONS

Baerlocher et al., Atlas of Zeolite Framework Types, Fifth Revised Edition, Elsevier Science B.V., (2001).
(Continued)

*Primary Examiner* — David M Brunsman
(74) *Attorney, Agent, or Firm* — Darryl M. Tyus

(57) ABSTRACT

A method of making a crystalline molecular sieve of MFI framework type, preferably ZSM-5, from a synthesis mixture comprising at least one source of tetravalent element (Y), at least one source of trivalent element (X), at least one source of alkali metal hydroxide (MOH), at least one struc-
(Continued)

ture directing; (R) and water, said synthesis mixture having the following molar composition: $YO_2$, $(p)X_2O_3$: (q) MOH: (r) R: (s) $H_2O$, wherein (p) is from 0.005 to 0.025, (q) is from 0.05 to 0.5, (r) is from 0.05 to 0.15 and (s) is from 35 to 45, wherein the ratio of the largest dimension (L) to the smallest dimension (S) of each crystal of the molecular sieve product is at least 5, and the smallest dimension (S) is from 20 nm to 200 nm.

18 Claims, 5 Drawing Sheets

(51) Int. Cl.
  *C07C 5/52* (2006.01)
  *B01J 20/18* (2006.01)
(52) U.S. Cl.
  CPC ...... *C07C 2529/44* (2013.01); *C07C 2529/46* (2013.01); *C07C 2529/48* (2013.01)

(56) References Cited

U.S. PATENT DOCUMENTS

| | | | |
|---|---|---|---|
| 4,585,638 | A | 4/1986 | Kühl |
| 5,240,892 | A | 8/1993 | Klocke |
| 7,074,384 | B2 | 7/2006 | Mertens et al. |

FOREIGN PATENT DOCUMENTS

| | | |
|---|---|---|
| FR | 2 387 908 | 11/1978 |
| JP | 2011-246339 | 12/2011 |
| WO | 97/03019 | 1/1997 |
| WO | 00/06492 | 2/2000 |
| WO | 2009/123796 | 10/2009 |
| WO | 2011/023360 | 3/2011 |

OTHER PUBLICATIONS

Caullet, et al. "*Synthesis of Zeolites in the Presence of Diquaternary Alkylammonium Ions as Structure-Directing Agents,*" Oil & Gas Science & Technology, vol. 62 (2007), No. 6, pp. 819-825.
Choi et al., Nature,"*Stable single-unit-cell nanosheets of zeolite MFI as active and long-lived catalysts,*" Nature, MacMillan Publishers, vol. 461 (2009) pp. 246-249.
Han et al., "*Zeolite Synthesis Using Flexible Diquaternary Alkylammonium Ions $(C_nH_{2n+1})_2HN^+ (CH_2)_5N^+ H(C_nH_{2n+1})_2$ with n=1-5 as Structure-Directing Agents,*" Chem. Mater., ACS (2005) 17, pp. 477-486.
Jackowski et al., "*Diquaternary Ammonium Compounds in Zeolite Synthesis: Cyclic and Polycyclic N-Heterocycles Connected by Methylene Chains,*" J. Am. Chem Soc. (2009) 131, pp. 1092-1100.
Liao et al. "*Synthesis, characterization of COK-5 with different Si/Al ratios and their catalytic properties for the tert-butylation of phenol,*" Microporous and Mesoporous Materials, Elsevier, Inc., 124 (2009), pp. 210-217.
Parikh et al., "*Non-thermal calcination by ultraviolet irradiation in the synthesis of microporous materials,*" Microporous and Mesoporous Materials, Elsevier Publishers, 76 (2004) pp. 17-22.
Serrano et al., "*Molecular and Meso- and Macroscopic Properties of Hierarchical Nanocrystalline ZSM-5 Zeolite Prepared by Seed Silanization,*" Chem. Mater. 21 (2009) pp. 641-654.
Periodic Table of the Elements, Chemical & Engineering News vol. 63, No. 5 (1985) p. 27.

MFI WITH UNUSUAL MORPHOLOGY

CROSS-REFERENCE TO RELATED APPLICATIONS

This application is a National Stage Application of International Application No. PCT/EP2013/073816, filed Nov. 14, 2013, and claims the benefit of and priority to U.S. Provisional Application Ser. No. 61/730,848, filed Nov. 28, 2012, EP Application No. 13153676.5, filed Feb. 1, 2013, and EP Application No. 13177993.6, filed Jul. 25, 2013, the contents of which are incorporated by reference in their entireties.

FIELD

This invention relates to a method of making a crystalline molecular sieve of MFI framework type, a crystalline molecular sieve of MFI framework type having platelet morphology, and a process for hydrocarbon conversion using said crystalline molecular sieves.

BACKGROUND

Crystalline ZSM-5 and its conventional preparation using tetrapropylammonium cations as a structure directing agent are taught by U.S. Pat. No. 3,702,886 and U.S. Pat. No. Re. 29,948. Conventional ZSM-5 has a distinctive X-ray diffraction pattern which distinguishes it from other known crystalline materials and is a highly versatile catalyst useful in a variety of organic conversion reactions. The unique framework type of ZSM-5 has been assigned the framework type MFI by the Structure Commission of the International Zeolite Association (see "Atlas of Zeolite Framework Types" C. Baerlocher, L. B. McCusker, D. H. Ohlson, Sixth Revised Edition 2007). Examples of other zeolites that have the MFI framework type include: AZ-1, encilite, FZ-1, LZ-105, mutinaite, NU-4, NU-5, silicalite (silica form of ZSM-5), TS-1, TSZ, TSZ-III, TZ-01, USC-4, USI-108, ZBH, ZKQ-1B, ZMQ-TB.

In addition to tetrapropylammonium cations, a large number of other organic nitrogen compounds, including certain diquaternary ammonium compounds, have been shown to direct the synthesis of ZSM-5. For example, U.S. Pat. No. 4,585,638 discloses that the synthesis of ZSM-5 can be directed by the diquaternary cation $(alkyl)_3N^+(CH_2)_6N^+(alkyl)_3$, where the alkyl group is propyl or butyl.

For some acid-catalyzed reactions over zeolites, it is beneficial to reduce diffusion lengths of the reagent and/or product molecules by employing a zeolite with a reduced crystal size. Small crystals also have the benefit of providing high surface area.

An example of small crystal ZSM-5 is disclosed in U.S. Pat. No. 5,240,892, in which the ZSM-5 is in the form of platelets having first and second major dimensions of at least about 0.05 micron, preferably at least about 0.1 micron, and a minor third dimension of less than about 0.02 micron, preferably less than about 0.01 micron. The ZSM-5 has a mesitylene sorption capacity of at least 3.0 weight % and is produced using precipitated silica as the silica source either in the absence of an organic directing agent or using n-propylamine as the directing agent.

In addition, in "Molecular and Meso- and Macroscopic Properties of Hierarchical Nanocrystalline ZSM-5 Zeolite Prepared by Seed Silanization", Chem. Mater. 21 (2009) 641-654, D. Serrano et al. report synthesizing ZSM-5 crystals as small as 5 to 10 nm using a dual template of tetrapropylammonium (TPA) ions and phenylaminopropyl-trimethoxysilane. In this method, the silanizing agent is introduced after the synthesis gel is pre-heated for short periods of time before the onset of zeolite crystallization.

Ryoo and coworkers have reported in "Stable single-unit-cell nanosheets of zeolite MFI as active and long-lived, catalysts", Nature 461, 246-249 (10 Sep. 2009), the synthesis of a single unit cell-thick version of ZSM-5 by using a single templating agent composed of a 22-carbon atom alkyl chain and two quaternary ammonium groups separated by a methylene chain of 6 carbon atoms. Here the quaternary ammonium groups are located within the single-unit cell nanosheets, which are separated from one another by the long alkyl chains.

In "Zeolite Synthesis Using Flexible Diquaternary Alkylammonium Ions $(C_nH_{2n+1})_2HN^+(CH_2)_5N^+H(C_nH_{2n+1})_2$ with n=1-5 as Structure-Directing Agents", Chem. Mater. 2005, 17, 477-486 (1 Jul. 2005), Han et al. report the use of $Et_6$-diquat-5 to produce ZSM-57 and the use of $Me_4$-diquat-5 to produce LEV and MCM-22.

Liao et al. report in "Synthesis, characterization of COK-5 with different Si/Al ratios and their catalytic properties for the tert-butylation of phenol", Microporous and Mesoporous Materials, 124 (2009) 210-217, the synthesis of COK-5 with $Et_6$-diquat-n (n=5, 6).

In "Diquaternary Ammonium Compounds in Zeolite Synthesis: Cyclic and Polycyclic N-Heterocycles Connected by Methylene Chains", J. Am. Chem. Soc. (2009), 131, 1092-1100, Jackowski et al. disclose MFI synthesis using N-heterocycle structure directing agents.

Caullet et al. report in "Synthesis of Zeolites in the Presence of Diquaternary Alkylammonium Ions as Structure-Directing Agents", Oil & Gas Science & Technology, Vol. 62 (2007), No. 6, pp. 819-825, the use of bis (n-trimethylaminoalkyl)ethers in the production of mainly ZSM-48 but also MFI type zeolite.

For several zeolites, and in particular those with the MFI structure, several morphologies are available with tunable crystal size for different applications. Examples of such morphologies are coffins, intergrown coffins, spheres and needles. In some cases however, it may be desirable to have the zeolite crystals with platelet morphology. Furthermore, for applications which can be limited by diffusion it is desirable to have small crystals. Crystal shape or morphology and size are thus important properties of molecular sieves.

The ability to control crystal shape and crystal size provides the ability to fine-tune a molecular sieve for specific applications in catalysis and molecular separations. Therefore, there is a need for a method to control the crystal size and morphology of MFI framework type molecular sieves, such as ZSM-5.

According to the present invention, using particular structure directing agents, it has now been found that new forms of crystalline molecular sieve with MFI framework type can be synthesized.

SUMMARY

In one aspect, the present invention provides a method of making a crystalline molecular sieve of MFI framework type, said method comprising the steps of: (a) providing a synthesis mixture comprising at least one source of tetravalent element (Y), at least one source of trivalent element (X), at least one source of alkali metal hydroxide (MOH), at least one structure-directing-agent (R) and water, said synthesis mixture having the following molar composition (expressed in terms of oxide):

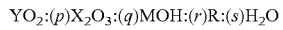

$YO_2:(p)X_2O_3:(q)MOH:(r)R:(s)H_2O$ wherein (p) is in the range from 0.005 to 0.025, (q) is in the range from 0.05 to 0.5, (r) is in the range from 0.05 to 0.15, (s) is in the range from 35 to 45; and wherein said structure directing agent (R) is a compound having a cation of the general formula $R^1R^2R^3N^+(CH_2)_nN^+R^4R^5R^6 A^-$ with n equal to 4, 5 or 6, $R^1$, $R^2$, $R^3$, $R^4$, $R^5$ and $R^6$ independently representing an alkyl group having 1 to 4 carbon atoms, and $A^-$ representing a hydroxide or a halogen; and
(b) treating said synthesis mixture under crystallization conditions to form crystals of molecular sieve of MFI framework type, wherein the ratio of the largest dimension (L) to the smallest dimension (S) of each crystal is at least 5, and the smallest dimension (S) is from 20 nm to 200 nm.

It is preferred when the structure directing agent is a N,N,N',N',N'-hexaethylpentane diammonium halide, most preferably the bromide.

In a further aspect of the present invention there is provided a crystalline molecular sieve of MFI framework type having a platelet morphology, wherein the ratio of the largest dimension (L) to the smallest dimension (S) of each crystal is at least 5 and the smallest dimension (S) is from 20 nm to 200 nm.

Preferably the molar ratio of silicon to aluminum is 15 to 70:1, most preferably 20 to 65:1.

In yet a further aspect of the present invention there is provided a process for hydrocarbon conversion comprising the step of contacting a hydrocarbon feedstock under hydrocarbon conversion conditions with the crystalline molecular sieve of MFI framework type of the present invention or a crystalline molecular sieve of MFI framework produced by the method of the present invention.

Preferably the crystalline molecular sieve of the present invention and that made by the method of the present invention is ZSM-5.

DETAILED DESCRIPTION OF THE EMBODIMENTS

Figure 1:
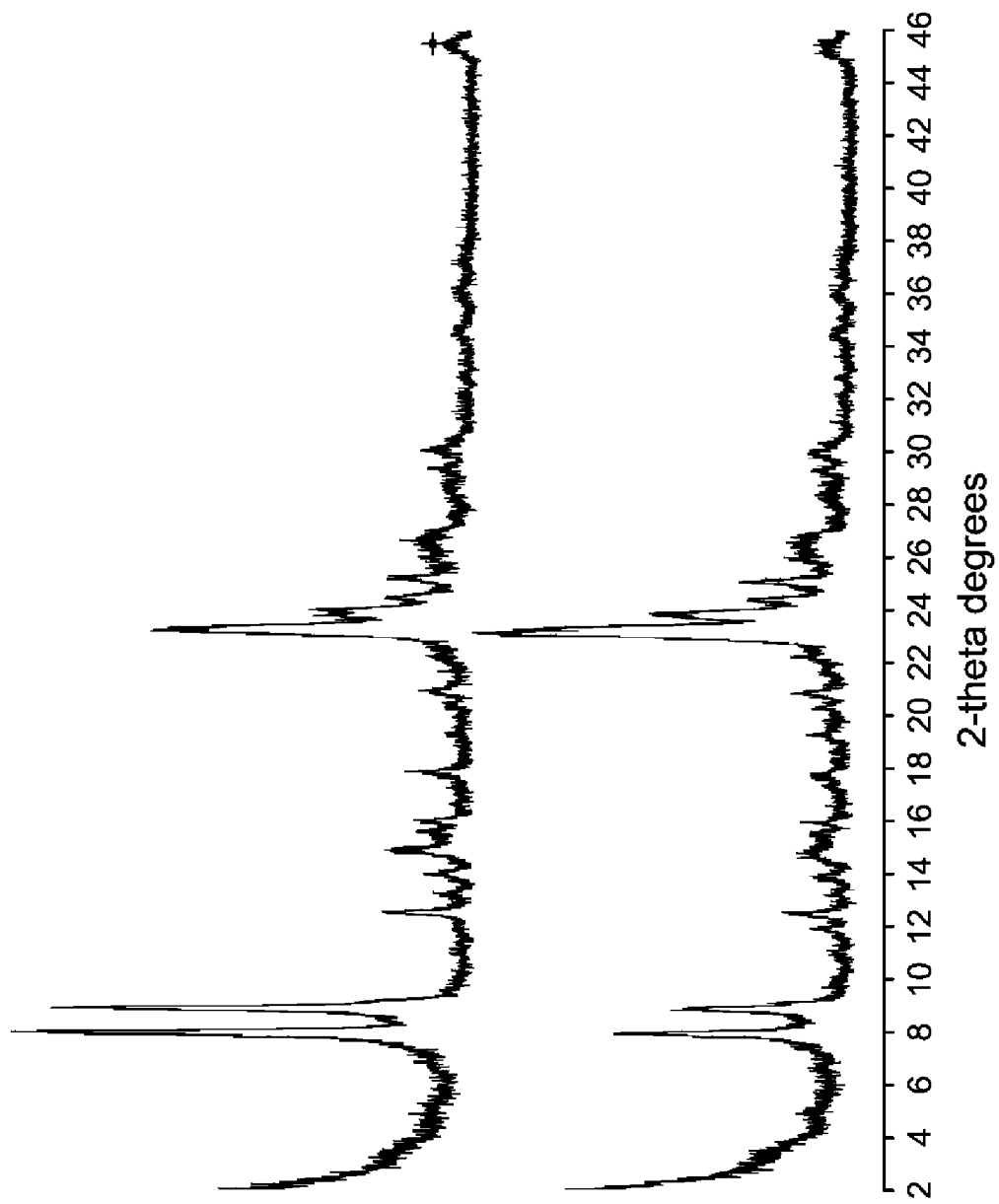
FIG. 1 shows the X-ray diffraction (XRD) pattern of a product made according to Example 1A, as synthesized (bottom curve) and after calcination at 550° C. (top curve).

Described herein is a process for the synthesis of a crystalline molecular sieve of the MFI framework type, using one or more of a specific series of diquaternary ammonium compounds as a structure directing agent. In some embodiments, the present process produces crystals of ZSM-5 with unusual platelet morphology.

The crystalline molecular sieves of the MFI framework type, and in particular ZSM-5 crystals, described herein are produced from a synthesis mixture comprising at least one source of tetravalent element (Y), at least one source of trivalent element (X), at least one source of alkali metal hydroxide (MOH), at least one structure-directing-agent (R) and water, the mixture having a composition, in terms of mole ratios of oxides, within the following ranges:

| Reactants | Useful | Preferred |
|---|---|---|
| $X_2O_3/YO_2$ (p) | 0.005 to 0.025 | 0.008 to 0.025 |
| $MOH/YO_2$ (q) | 0.05 to 0.5 | 0.2 to 0.4 |
| $R/YO_2$ (r) | 0.05 to 0.15 | 0.08 to 0.1 |
| $H_2O$ (s) | 35 to 45 | 39 to 41 |

Suitable sources of the tetravalent element Y depend on the element Y. Preferably, Y is selected from silicon, germanium and mixtures thereof. Examples of suitable sources of silicon and/or germanium include colloidal suspensions of silica, alkali metal silicates, tetra-alkyl orthosilicates and germanium oxide. The trivalent element X is selected from aluminum, boron, gallium and mixtures thereof, but is preferably aluminum. Suitable sources of aluminum include hydrated alumina and water-soluble aluminum salts, such as aluminum nitrate. Other sources of aluminum may include clays or treated clays such as metakaolin. Combined sources of X and Y including aluminosilicate zeolites such as zeolite Y may also be used.

In the present synthesis method, the alkali metal (M) is selected from the group consisting of sodium, potassium and mixtures thereof. Preferably M comprises sodium. The sodium source may be sodium hydroxide or sodium aluminate. The potassium source may be potassium hydroxide.

Suitable sources of R include hydroxides and/or halides of the relevant diquaternary ammonium compounds. The structure directing agent is a compound having a cation of the general formula $R^1R^2R^3N^+(CH_2)_nN^+R^4R^5R^6 A^-$ with n equal to 4, 5 or 6, $R^1$, $R^2$, $R^3$, $R^4$, $R^5$ and $R^6$ independently representing an alkyl group having 1 to 4 carbon atoms, and $A^-$ representing a hydroxide or a halide ion. Preferably, n equals 5. Another preferred embodiment is that $R^1$ to $R^6$ independently represent methyl or ethyl, most preferably ethyl. The most preferred structure directing agent (R) is a N,N,N,N',N',N'-hexaethylpentane diammonium dihalide, most preferably the dibromide.

The synthesis mixture may also comprise seed crystals, such as, for example, small crystals of molecular sieve having the same or a different framework type than the desired molecular sieve. The use of seeds in a molecular sieve synthesis mixture has beneficial effects, for example, in controlling the particle size of the product, accelerating synthesis and improving the proportion of product that is of the intended framework type.

Under crystallization conditions, crystals of molecular sieve of MFI framework type with unusual platelet morphology can be made, wherein the ratio of the largest dimension (L) to the smallest dimension (S) of each crystal is at least 5, and the smallest dimension (S) is from 20 nm to 200 nm. In the present invention, crystals of molecular sieve of MFI framework type with platelet morphology typically are in the form of crystals having two large dimensions (length and width) and a third small dimension (thickness), the two larger (basal) dimensions being substantially the same. In the present invention, the largest dimension (L) of a platelet corresponds to its length and the smallest dimension (S) of a platelet corresponds to its thickness. Said largest dimension (L) and smallest dimension (S) are determined by scanning electron microscopy (SEM). In the present invention, it is especially preferred that said definitions of the smallest dimension (S) and of the ratio of the largest dimension (L) to the smallest dimension (S) apply independently to each crystal. The molar ratio of silicon to aluminum for the crystalline molecular sieve of the present invention is preferably 15 to 70:1, and most preferably 20 to 65:1.

Crystallization from the above synthesis mixture can be carried out under either static or stirred conditions in a suitable reactor vessel, such as for example, polypropylene jars or teflon lined or stainless steel autoclaves. Crystallization conditions include a temperature of about 90° C. to about 200° C., with a preferred temperature range of 155° C. to 185° C., for a time sufficient for crystallization to occur at the temperature used. Preferably, this would be for 24 to 240 hours and most preferably 96 to 240 hours. Thereafter, the crystals are separated from the liquid and recovered.

The as-synthesized molecular sieve usually contains alkali metal ions. To the extent desired and depending on the $X_2O_3/YO_2$ molar ratio of the material, any alkali metal cations in the as-synthesized MFI type molecular sieve can be replaced in accordance with techniques well known in the art, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The as-synthesized crystals may also be subjected to treatment to remove part or all of the organic structure directing agent R used in its synthesis. This is conveniently effected by thermal treatment in which the as-synthesized material is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. Alternatively, the organic structure directing agent R can be removed by treatment with ozone (see, e.g., Parikh et al., Microporous and Mesoporous Materials 76 (2004) 17-22). The organic-free product, especially in its metal, hydrogen and ammonium forms, is particularly useful in the catalysis of certain organic, e.g., hydrocarbon, conversion reactions.

The present molecular sieve may be intimately combined with a hydrogenating component, such as molybdenum, rhenium, nickel, cobalt, chromium, manganese, or a noble metal such as platinum or palladium where a hydrogenation-dehydrogenation function is to be performed. Such component can be in the composition by way of co-crystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The present molecular sieve, when employed either as an adsorbent or as a catalyst should be dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the molecular sieve in a vacuum, but a longer time is required to obtain a sufficient amount of dehydration.

The crystalline molecular sieves described herein can be used as an adsorbent or as a catalyst to catalyze a wide variety of organic compound conversion processes including many of present commercial/industrial importance. Examples of organic compound conversion processes which are effectively catalyzed by the present molecular sieve are those where high acid activity and large surface area are important.

As in the case of many catalysts, it may be desirable to incorporate the present molecular sieve with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the present molecular sieve, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the present molecular sieve include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the molecular sieve also include inorganic oxides, such as silica, zirconia, titania, magnesia, beryllia, alumina, and mixtures thereof.

In addition to the foregoing materials, the present molecular sieve can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of the molecular sieve and inorganic oxide matrix may vary widely, with the molecular sieve content ranging from about 1 to about 90 percent by weight and more usually, particularly when the composite is prepared in the form of beads, in the range of about 2 to about 80 weight percent of the composite.

The invention will now be more particularly described with reference to the following Examples and the accompanying drawings.

Example 1A

A synthesis mixture with the following molar composition was prepared with a $Si/Al_2$ ratio of 75:

0.25NaOH/0.09R/0.013Al$_2$O$_3$/SiO$_2$/40H$_2$O

Figure 2A:
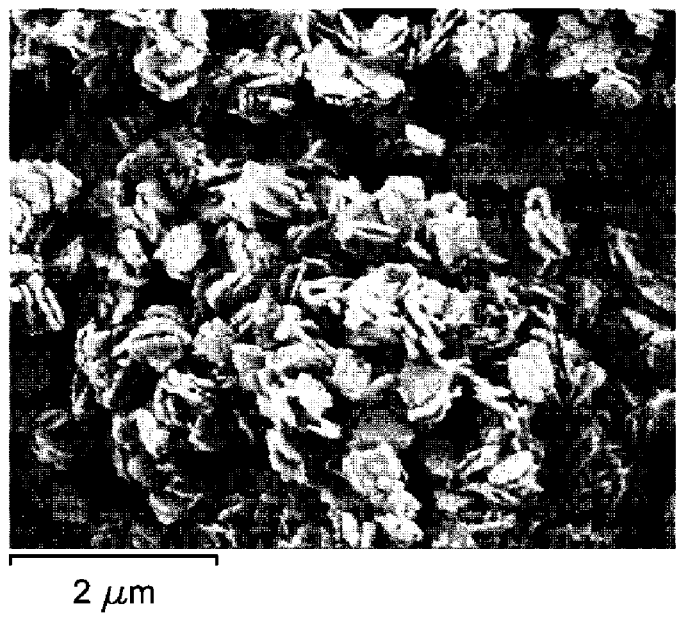
FIG. 2A provides a scanning electron microscope (SEM) picture of a product made according to Example 1A.

The structure directing agent used, R, was 1,5-bis(triethylammonium)pentane dibromide. A first mixture was made by combining 18.03 parts of the silica source Cab-o-Sperse 2017A (an aqueous dispersion of fumed silica, available from Cabot, containing 10 wt % of $SiO_2$ and 0.15 parts of a 40 wt % solution of NaOH). This mixture was homogenized and loaded into an autoclave and heated for 16 hours at 100° C. After cooling to room temperature, this mixture was transferred to a mixing vessel and 0.15 parts by weight of a 40 wt % solution of NaOH was added and mixed. To the resulting mixture were added and mixed 1.38 parts of deionized water. Then 0.67 parts by weight of a 40 wt % solution of aluminosulphate hydrate [$Al_2(SO_4)_3 \cdot 18H_2O$] were added and mixed. Into this mixture 4.67 parts by weight of a 25 wt % solution of the 1,5-bis(triethylammonium)pentane dibromide were added followed by the addition of 0.13 parts of a slurry containing 35 wt % of ZSM-5 seeds. These seeds were prepared according to the procedure described in WO 97/03019. The resulting mixture was homogenized before loading into an autoclave. This autoclave was heated to 160° C. for 120 hours with stirring. After crystallization the solids were recovered, washed and dried and the XRD pattern was recorded. FIG. 1 shows the XRD patterns for the as-synthesized product and for the product after calcination at 550° C. FIG. 2A shows the SEM picture of the product. The crystals are thin platelets of about 0.5 micron in size and a thickness around 100 nm. The $Si/Al_2$ molar ratio of the product as determined by ICP (Inductive Coupling Plasma) spectroscopy was 76.3.

Example 1B: Effect of NaOH/SiO$_2$

A synthesis mixture with the following molar composition was prepared in the same way as in Example 1A, using the same ingredients, except the proportion of ingredients was such that the synthesis mixture had the following molar composition:

0.20NaOH/0.09R/0.013Al$_2$O$_3$/SiO$_2$/40H$_2$O

Figure 2B:
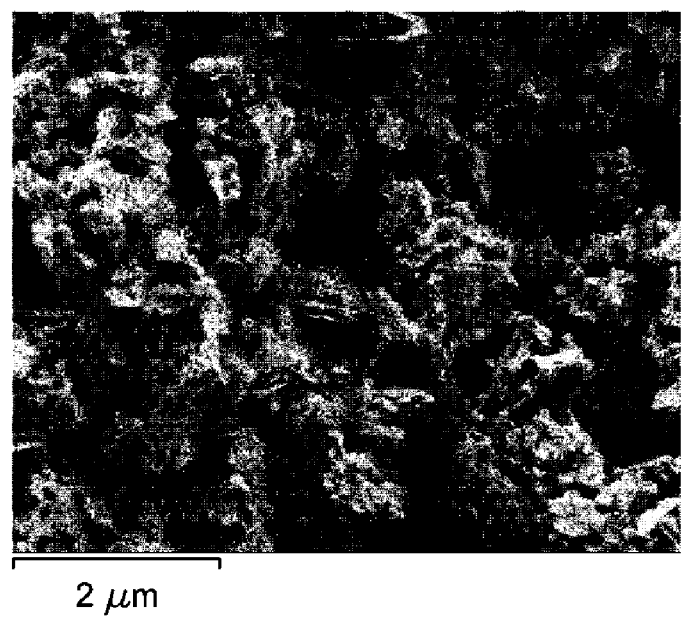
FIG. 2B shows the SEM picture of a product made according to Example 1B.

A SEM picture of the obtained product is shown in FIG. 2B. The crystal morphology is somewhat less defined as to the product of Example 1A.

Example 2: Effect of Silica Source

A mixture with the same molar composition as in Example 1B was prepared but using Ultrasil VN (precipitated silica available from Evonik) as an alternative silica source and crystallized under the same conditions.

Figure 3:
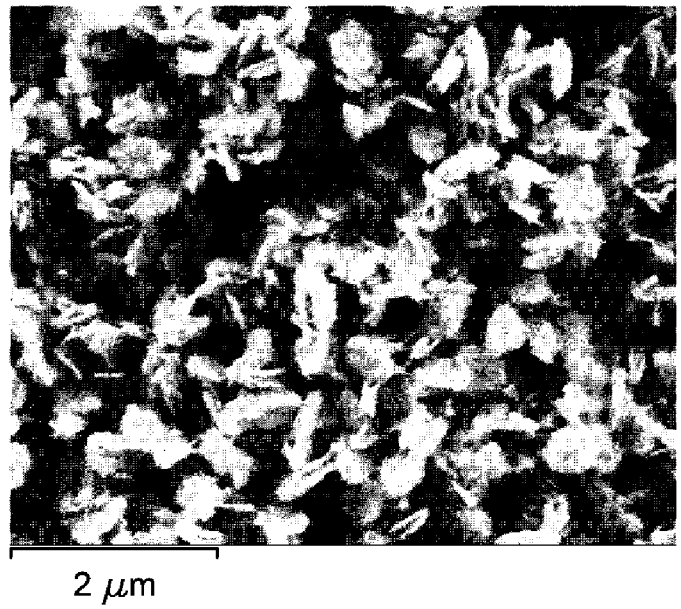
FIG. 3 shows the SEM picture of a product made according to Example 2.

The material was dried and the XRD pattern was the same as the product made in Example 1. The SEM is presented in FIG. 3. It can be seen that the change of silica source resulted in thinner crystals.

Example 3: Effect of Higher Crystallization Temperature

Figure 4:
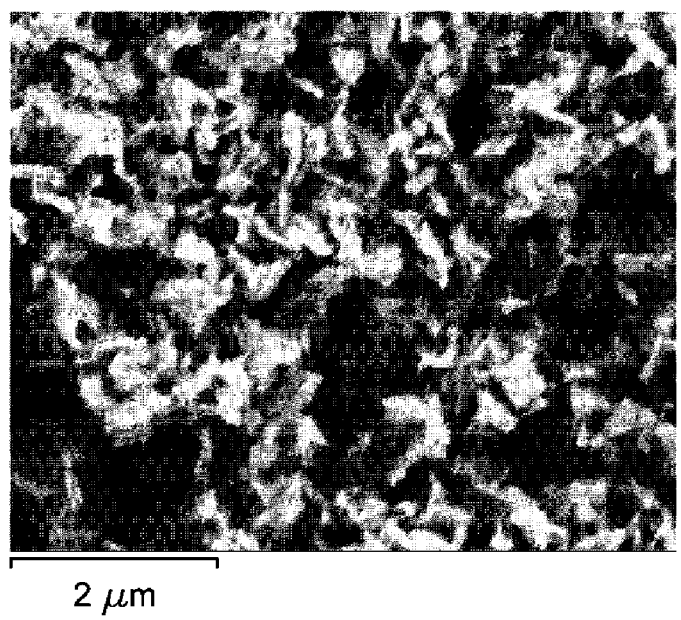
FIG. 4 shows the SEM picture of a product made according to Example 3.

A mixture with the same composition and ingredients as in Example 1A was crystallized at 180° C. while stirring. After 144 hours at crystallization temperature, the reactor was cooled to room temperature and the solids recovered and washed using the centrifuge. The material was dried and the XRD pattern was the same as the product made in Example 1. A SEM picture is presented in FIG. 4. It can be seen that the change in temperature has a similar effect as changing the silica source: the higher temperature results in thinner crystals.

Examples 4 to 7: Effect of Seeding Level

Figure 5:
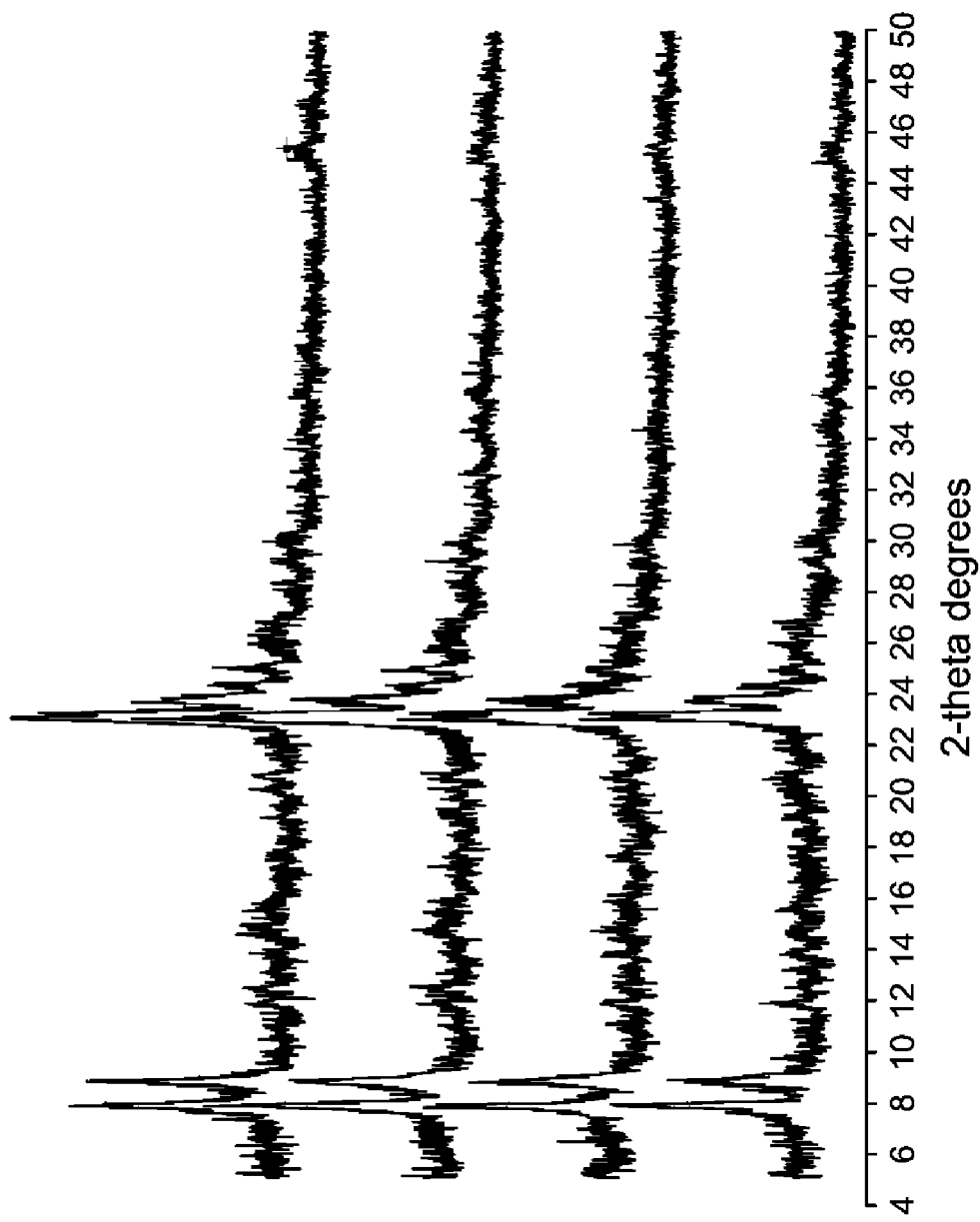
FIG. 5 shows the XRD pattern of a product made according to Examples 4 (top) to 7 (bottom).
Figure 6:
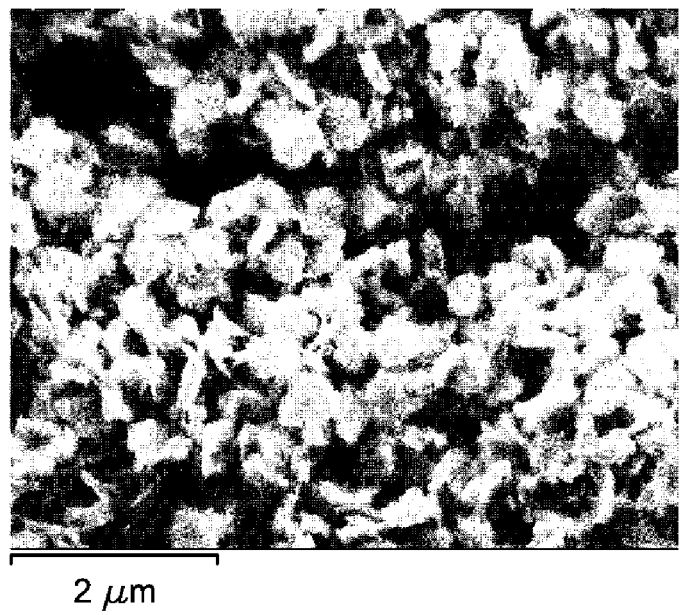
FIG. 6 shows the SEM picture of a product made according to Example 4.
Figure 7:
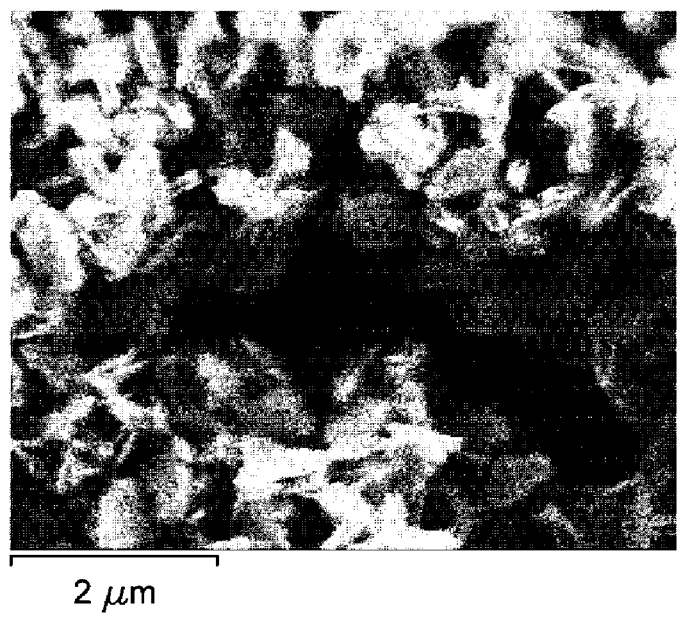
FIG. 7 shows the SEM picture of a product made according to Example 6.

Four mixtures were prepared according to the procedure and composition of Example 1A. Each of them was however seeded with a different amount of seeds of molecular sieves having the MFI framework type and was crystallized under stirred conditions at 165° C. for 144 hours. Table 1 below summarizes the different conditions for the various Examples. The XRD patterns of the different materials obtained after washing and drying, are shown in FIG. 5. All materials were identified as zeolites with the MFI framework type, regardless of the seeding level. In FIG. 6 a SEM picture of the product made in the presence of 0.15 wt % seeds is shown; FIG. 7 is a SEM picture of the material made with 0.05 wt % seeds. By comparison of both pictures, it can be seen that the reduction of the seeding level resulted in larger platelets but with similar thickness.

Examples 8 to 19: Effect of Si/Al$_2$ Ratio of Synthesis Mixture

The synthesis mixtures with the following molar compositions were all prepared according to the same procedure and the same raw materials:

$x$NaOH/0.09R/$y$Al$_2$O$_3$/SiO$_2$/40H$_2$O with structure directing agent R=1,5bis(triethylammonium) pentane dibromide. A first mixture was made by combining the silica source Cab-o-Sperse 2017A (containing 10 wt % of $SiO_2$) and the appropriate amount of the 40 wt % solution of NaOH. This mixture was homogenized and loaded to an autoclave and heated during 16 hours at 100° C. After cooling to room temperature, this mixture was transferred to a mixing vessel and a second amount of 40 wt % solution of NaOH was added and mixed. To the resulting mixture was added the appropriate amount of deionized water. Then the appropriate amount of the 40 wt % solution of aluminosulphate hydrate ($Al_2(SO_4)_3 \cdot 18H_2O$) was added and mixed. Into this mixture, the structure directing agent R=1,5bis (triethylammonium) pentane dibromide was added followed by the addition of a slurry containing 35 wt % of ZSM-5 seeds (seeding level 2000 wt ppm). These seeds were prepared according to the procedure described in WO 97/03019. The resulting mixture was homogenized before loading into an autoclave. This autoclave was heated to 170° C. during 144 hours with stirring. After crystallization, the solids were recovered, washed and dried and an XRD pattern was recorded. All products were ZSM-5. Table 1

TABLE 1

| Ex. | Silica source | Si/Al$_2$ | NaOH/Si | Wt. % seeds | Temp ° C. | Time hr |
|---|---|---|---|---|---|---|
| 1A | Cab-o-Sperse | 75 | 0.25 | 0.15 | 160 | 120 |
| 1B | Cab-o-Sperse | 75 | 0.20 | 0.15 | 160 | 120 |
| 2 | Ultrasil | 75 | 0.25 | 0.15 | 160 | 144 |
| 3 | Cab-o-Sperse | 75 | 0.25 | 0.15 | 180 | 144 |
| 4 | Cab-o-Sperse | 75 | 0.25 | 0.15 | 165 | 144 |
| 5 | Cab-o-Sperse | 75 | 0.25 | 0.10 | 165 | 144 |
| 6 | Cab-o-Sperse | 75 | 0.25 | 0.05 | 165 | 144 |
| 7 | Cab-o-Sperse | 75 | 0.25 | 0.01 | 165 | 144 |
| 8 | Cab-o-Sperse | 75 | 0.20 | 0.02 | 170 | 144 |
| 9 | Cab-o-Sperse | 90 | 0.20 | 0.02 | 170 | 144 |
| 10 | Cab-o-Sperse | 100 | 0.20 | 0.02 | 170 | 144 |
| 11 | Cab-o-Sperse | 120 | 0.20 | 0.02 | 170 | 144 |
| 12 | Cab-o-Sperse | 75 | 0.25 | 0.02 | 170 | 144 |
| 13 | Cab-o-Sperse | 90 | 0.25 | 0.02 | 170 | 144 |
| 14 | Cab-o-Sperse | 100 | 0.25 | 0.02 | 170 | 144 |
| 15 | Cab-o-Sperse | 120 | 0.25 | 0.02 | 170 | 144 |
| 16 | Cab-o-Sperse | 45 | 0.40 | 0.02 | 170 | 144 |
| 17 | Cab-o-Sperse | 50 | 0.40 | 0.02 | 170 | 144 |
| 18 | Cab-o-Sperse | 55 | 0.40 | 0.02 | 170 | 144 |
| 19 | Cab-o-Sperse | 60 | 0.40 | 0.02 | 170 | 144 |

We claim:

1. A method of making a crystalline molecular sieve of MFI framework type, said method comprising the steps of:
   (a) providing a synthesis mixture comprising at least one source of tetravalent element (Y), at least one source of trivalent element (X), at least one source of alkali metal hydroxide (MOH), at least one structure directing agent (R) and water, said synthesis mixture having the following molar composition (expressed in terms of oxide):

YO$_2$:($p$)X$_2$O$_3$:($q$)MOH:($r$)R:($s$)H$_2$O

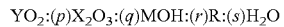

wherein (p) is in the range from 0.005 to 0.025, (q) is in the range from 0.05 to 0.5, (r) is in the range from 0.05 to 0.15, (s) is in the range from 35 to 45; and wherein said structure directing agent (R) is a compound having a cation of the general formula R$^1$R$^2$R$^3$N$^+$(CH$_2$)$_n$N$^+$R$^4$R$^5$R$^6$A$^-$ with n equal to 4, 5 or 6, R$^1$, R$^2$, R$^3$, R$^4$, R$^5$ and R$^6$ independently representing an alkyl group having 1 to 4 carbon atoms, and A$^-$ representing a hydroxide or a halide ion, wherein said tetravalent element is silicon, and said silicon is in the form of a fumed silica or a precipitated silica; and
   (b) treating said synthesis mixture under crystallization conditions to form crystals of molecular sieve of MFI framework type, wherein the ratio of the largest dimension (L) to the smallest dimension (S) of each crystal is at least 5, and the smallest dimension (S) is from 20 nm to 200 nm, wherein said crystallization conditions comprise a temperature in the range of 90 to 200° C. applied for 24 to 240 hours.

2. The method of claim 1, wherein (p) is in the range from 0.008 to 0.025.

3. The method of claim 1, wherein (q) is in the range from 0.2 to 0.4.

4. The method of claim 1, wherein (r) is in the range from 0.08 to 0.1.

5. The method of claim 1, wherein (s) is in the range from 39 to 41.

6. The method of claim 1, wherein said trivalent element is aluminum, boron, gallium or a mixture thereof.

7. The method of claim 1, wherein said alkali metal (M) is sodium.

8. The method of claim 1, wherein n equals 5.

9. The method of claim 1, wherein R$^1$ to R$^6$ independently represent methyl or ethyl.

10. The method of claim 1, wherein said structure directing agent (R) is a N,N,N,N',N',N'-hexaethylpentane diammonium halide.

11. The method of claim 1, wherein said crystallization conditions comprise a temperature in the range of 155° C. to 185° C.

12. The method of claim 1, wherein said synthesis mixture further comprises seed crystals.

13. The method of claim 1, wherein said crystalline molecular sieve of MFI framework type is ZSM-5.

14. A crystalline molecular sieve of MFI framework type comprising silicon and aluminum and having a platelet morphology, wherein the ratio of the largest dimension (L) to the smallest dimension (S) of each crystal is at least 5, and the smallest dimension (S) is in the range from 20 nm to 200 nm,
   wherein said crystalline molecular sieve made by the method comprising the steps of:
   (a) providing a synthesis mixture comprising at least one source of tetravalent element (Y), at least one source of trivalent element (X), at least one source of alkali metal hydroxide (MOH), at least one structure directing agent (R) and water, said synthesis mixture having the following molar composition (expressed in terms of oxide):

YO$_2$:($p$)X$_2$O$_3$:($q$)MOH:($r$)R:($s$)H$_2$O wherein (p) is in the range from 0.005 to 0.025, (q) is in the range from 0.05 to 0.5, (r) is in the range from 0.05 to 0.15, (s) is in the range from 35 to 45; and wherein said structure directing agent (R) is a compound having a cation of the general formula R$^1$R$^2$R$^3$N$^+$(CH$_2$)$_n$N$^+$R$^4$R$^5$R$^6$A$^-$ with n equal to 4, 5 or 6, R$^1$, R$^2$, R$^3$, R$^4$, R$^5$ and R$^6$ independently representing an alkyl group having 1 to 4 carbon atoms, and A$^-$ representing a hydroxide or a halide ion, wherein said tetravalent element is silicon, and said silicon is in the form of a fumed silica or a precipitated silica; and

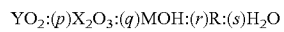

(b) treating said synthesis mixture under crystallization conditions to form crystals of molecular sieve of MFI framework type, wherein the ratio of the largest dimension (L) to the smallest dimension (S) of each crystal is at least 5, and the smallest dimension (S) is from 20 nm to 200 nm, wherein said crystallization conditions comprise a temperature in the range of 90 to 200° C. applied for 24 to 240 hours.

15. The crystalline molecular sieve of claim 14, wherein having a molar ratio of silicon to aluminum in the range from 15:1 to 70:1.

16. The crystalline molecular sieve of claim 15, wherein said crystalline molecular sieve of MFI framework type is ZSM-5.

17. A process for hydrocarbon conversion comprising the step of contacting a hydrocarbon feedstock under hydrocarbon conversion conditions with the crystalline molecular sieve of MFI framework type of claim 14.

18. The process of claim 17, wherein said crystalline molecular sieve of MFI framework type is ZSM-5.

* * * * *

UNITED STATES PATENT AND TRADEMARK OFFICE
CERTIFICATE OF CORRECTION

PATENT NO.        : 9,725,327 B2
APPLICATION NO.   : 14/440946
DATED             : August 8, 2017
INVENTOR(S)       : Machteld Maria Wilfried Mertens et al.

It is certified that error appears in the above-identified patent and that said Letters Patent is hereby corrected as shown below:

On the Title Page

Item (71) should read:
"Applicants: ExxonMobil Chemical Patents Inc., Baytown, TX (US)".

Signed and Sealed this
Sixth Day of February, 2018

Joseph Matal
*Performing the Functions and Duties of the*
*Under Secretary of Commerce for Intellectual Property and*
*Director of the United States Patent and Trademark Office*